United States Patent
Schöbel (nee Bauer) et al.

(10) Patent No.: US 7,775,210 B2
(45) Date of Patent: Aug. 17, 2010

(54) NASAL CANNULA

(76) Inventors: Ulla Schöbel (nee Bauer), Schillerstr. 19, 06366 Koethen (DE); Silvio Kilz, Adam-Weise-Str. 32, 06773 Graefenhainichen (DE); Ingo Müller, Helene-Meier-Str. 9, 06844 Dessau (DE); Martin Baecke, Lindenstr. 7, 06847 Dessau (DE); Heiko Krause, Windmuehlenstr. 43, 06846 Dessau (DE)

( * ) Notice: Subject to any disclaimer, the term of this patent is extended or adjusted under 35 U.S.C. 154(b) by 651 days.

(21) Appl. No.: 11/879,027

(22) Filed: Jul. 13, 2007

(65) Prior Publication Data

US 2007/0283957 A1    Dec. 13, 2007

Related U.S. Application Data

(63) Continuation of application No. PCT/DE2005/002335, filed on Dec. 30, 2005.

(30) Foreign Application Priority Data

Jan. 7, 2005    (DE) .................... 10 2005 000 922

(51) Int. Cl.
*A61M 11/00* (2006.01)
(52) U.S. Cl. .................. 128/207.18; 128/204.17
(58) Field of Classification Search ............ 128/204.17, 128/204.18, 207.18

See application file for complete search history.

(56) References Cited

U.S. PATENT DOCUMENTS

2009/0056717 A1*  3/2009  Richards et al. ........ 128/204.17

FOREIGN PATENT DOCUMENTS

WO    WO 02/002413 A2    8/2002

* cited by examiner

*Primary Examiner*—Steven O Douglas
(74) *Attorney, Agent, or Firm*—Clement Cheng

(57) ABSTRACT

The invention relates to a nasal cannula for an anti-snoring apparatus, comprising a forked tube pneumatically connected to apertures, which are embodied and positioned in such a way that air can be administered into the nose of a user via these apertures. The nasal cannula further comprises a heating wire extending in the interior of forked tube in such a way that the heating wire can heat the air supplied through the forked tube. The invention moreover relates to a nosepiece and to a Y-shaped element for nasal cannula including internal radius steps at tube connection points. The invention further relates to a nosepiece and to a Y-shaped element having rounded off transition regions. The invention finally relates to a method for avoiding condensation in nasal cannulas. To this end, the gas is heated as it flows through the tubes of a nasal cannula.

31 Claims, 4 Drawing Sheets

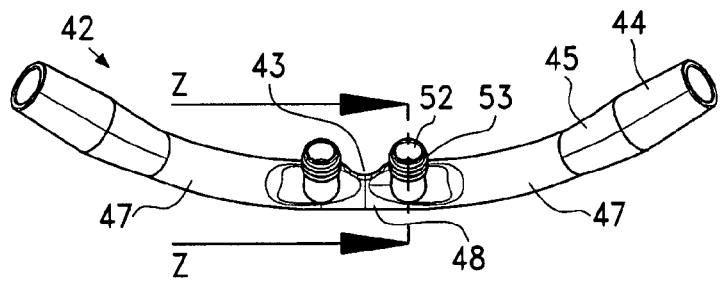
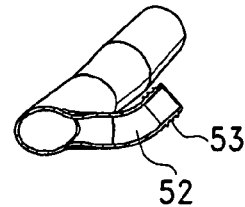
FIG.7  FIG.8
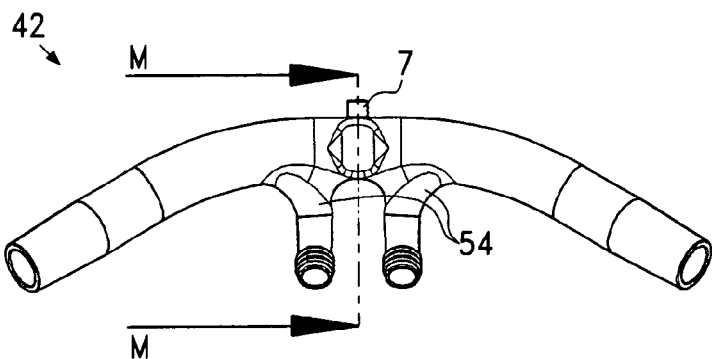
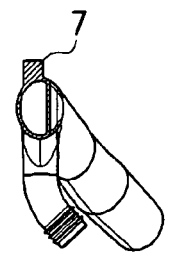
FIG.9  FIG.10
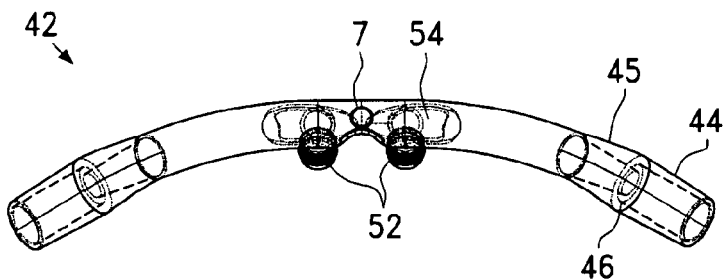
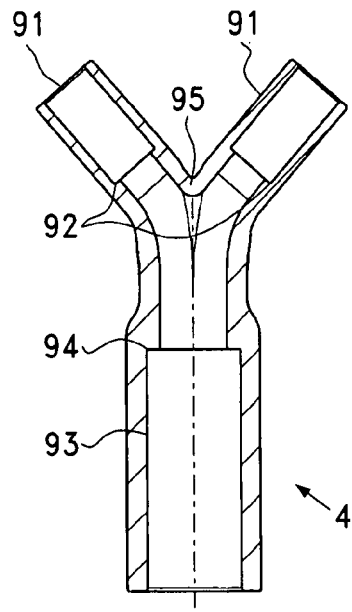
FIG.11  FIG.12

NASAL CANNULA

This application claims priority from PCT application PCT/DE2005/002335 having publication number WO 2006/072231 entitled Air Glasses, Nosepiece, Y-Shaped Element And Corresponding Method by inventors BAUER, KILZ, and MULLER. This application is a continuation of international application number PCT/DE2005/002335 (publication number: WO 2006/072231 A2) filed on Dec. 30, 2005 and entitled AIR GLASSES, NOSEPIECE, Y-SHAPED ELEMENT AND CORRESPONDING METHOD and claims the benefit of the above-mentioned international application and the corresponding German national patent application number 10 2005 000 922.0 filed on Jan. 7, 2005 and entitled LUFTBRILLE, NASENSTÜCK, Y-STÜCK SOWIE VERFAHREN the contents of which are expressly incorporated herein by reference.

FIELD OF THE INVENTION

The invention relates to wearable respiration devices, more specifically to air glasses apparatus, nasal cannula, nosepiece, Y-shaped element and corresponding method. Specifically, the invention relates to constructive modifications to facilitate the use of nasal cannulas for pneumatically splinting the upper respiratory tract.

DISCUSSION OF RELATED ART

Obstructive respiratory disorders lead to apneas (respiratory arrest) making the sleeping person wake up. Frequent apneas prevent the sleeping person from falling into the restful deep sleep. Persons suffering from apneas during sleep are, therefore, tired in the daytime, which may result in social problems at the workplace and, in the worst case, in fatal accidents, e.g. of professional drivers.

Apparatus for performing the CPAP (continuous positive airway pressure) therapy are known from the prior art. The CPAP therapy is described in more detail in Chest. Vol. 110, pages 1077 to 1088, October 1996 and in Sleep, Vol. No. 19, pages 184 to 188.

In the CPAP therapy the patient is supplied with a constant positive pressure via a nose mask so as to splint the upper respiratory tract. The correct choice of the positive airway pressure ensures that the upper respiratory tract remains fully opened during the whole night, so that no obstructive respiratory disorders will occur. Bi-level apparatus were developed, inter alia, to increase the comfort, which reduce the pressure during the respiratory break. The term PAP apparatus is here used as generic term for apparatus that pneumatically splint the upper respiratory tract.

Snoring and apneas may have one and the same cause, that is, too slack a palatal and tongue tissue.

Moreover, oxygen cannulas for the oxygen treatment are known from the prior art. The oxygen cannulas are used to provide the patient with air having an increased partial pressure of oxygen (>210 in bar) or pure oxygen through the nose. An oxygen treatment takes place, for example, in the case of acute or chronic hypoxemia as a result of respiratory or cardiac/circulatory disorders (myocardial infarction, shock) or certain poisonings, e.g. through carbon monoxide, carbon dioxide, illuminating gas or smoke.

The use of oxygen cannulas in an anti-snoring apparatus is known from WO 02/062413 A2 (HEW01). In this connection, oxygen cannulas are designated as nasal cannulas.

Vapotherm 2000i is a humidifying system, which delivers airflows in the range of 8 to 40 l/min via a nasal cannula to patients. The delivered air is humidified and heated. Air may be accumulated with oxygen.

It is the object of the invention to provide a nasal cannula, a nosepiece, a Y-shaped element as well as a method, which are specifically well suited to pneumatically splint the upper respiratory tract.

SUMMARY OF THE INVENTION

The heating of a forked tube by means of a heating wire can prevent the condensation of humidity in the forked tube. A laying of the heating wire in the interior of the forked tube is simple under the aspect of production engineering. Because of the heat release to the ambiance of the forked tube the temperature in the forked tube drops approximately linearly with the distance from the compressor. This temperature drop may be compensated by a constant heating power per unit of length, such as one generated by the heating wire. In dependence on the construction of the tube the necessary heating power can be kept under 15 watt for the entire nasal cannula. In other cases, legal provisions would demand the use of fire-retarding plastics, which are generally not biocompatible and the use of which in medical engineering products is therefore problematical.

A temperature measurement of the administered air allows to control the heating power of a heating wire or a heater in a compressor casing in such a way that the temperature is comfortable for the user. Without a compensation of the temperature drop in the forked tube the application apertures in the prongs would be the coldest spots. Consequently, this is where humidity is condensed most. For this reason, a control of the heating power based on a temperature measurement in the proximity of the application apertures is suited best to prevent a condensation in the entire nasal cannula.

For reasons of material saving it is desirable that the temperature sensor be read out via the heating wire. Due to the progress made in the integration of circuits it is possible to produce digital temperature sensors of an acceptable size, which modulate their sensor signal onto the heating wire.

The deviation of the outer shell of the insulation of the heating wire from the usual cylindrical shape due to elevations and recesses prevents too strong a reduction of the airflow through the forked tube if the forked tube is kinked. In such a case there is the danger that the heating wire is overheated at the kink site and melts into the forked tube because of the insufficient cooling of the heating wire at the kink site.

If the forked tube is kinked, elevations and recesses extending along the heating wire are particularly suited to ensure a sufficient airflow. A triangular cross-section of the elevations advantageously provides that the contact surface between the insulation of the heating wire and the inside of the forked tube is kept small during both normal operation and kinking. The overall star-shaped cross-section of the insulation advantageously enlarges the surface of the insulation and thus provides for a reduction of the thermal resistance between the insulation and the air flowing past.

Also projections extending in the longitudinal direction of the forked tube advantageously make sure that there is a sufficient airflow, inter alia, for cooling the heating wire, even if the forked tube is kinked.

Stabilizing wires serve to reduce a longitudinal expansion of the tubes.

The mechanical connection of two elements of the forked tube at their connector-sided end allows the saving of a Y-shaped element or the integration of the same in the connector. This advantageously results in a reduction of the sound emission because the Y-shaped element integrated in the connector is farther away from the application apertures.

Internal radius steps at different connection points can just about compensate the thickness of the tube, so that the transition between the tube and the corresponding component is even upon fixing the tube. An even transition is subject to fewer whirls and, thus, to less sound.

Also, the transition regions between a prong and the central connection piece as well as between a prong and the connection piece on the side of the prong are rounded off so as to advantageously prevent the formation of whirls and, thus, an emission of noise.

An indentation in the central connection piece allows the adjustment of an optimum flow resistance of the connection piece.

A preferred embodiment of the invention will be explained in more detail below with reference to the accompanying drawings.

BRIEF DESCRIPTION OF THE DRAWINGS

FIG. 7 shows a perspective view of a second embodiment of a nosepiece from a first direction.

FIG. 8 shows a section through a prong along Z-Z.

FIG. 9 shows a perspective view of the second embodiment of the nosepiece from a second direction.

FIG. 10 shows a section along M-M.

FIG. 11 shows a perspective view of the second embodiment of the nosepiece from a third direction.

FIG. 12 shows a Y-shaped element for nasal cannulas according to the invention.

DETAILED DESCRIPTION OF THE PREFERRED EMBODIMENT

Figure 1:
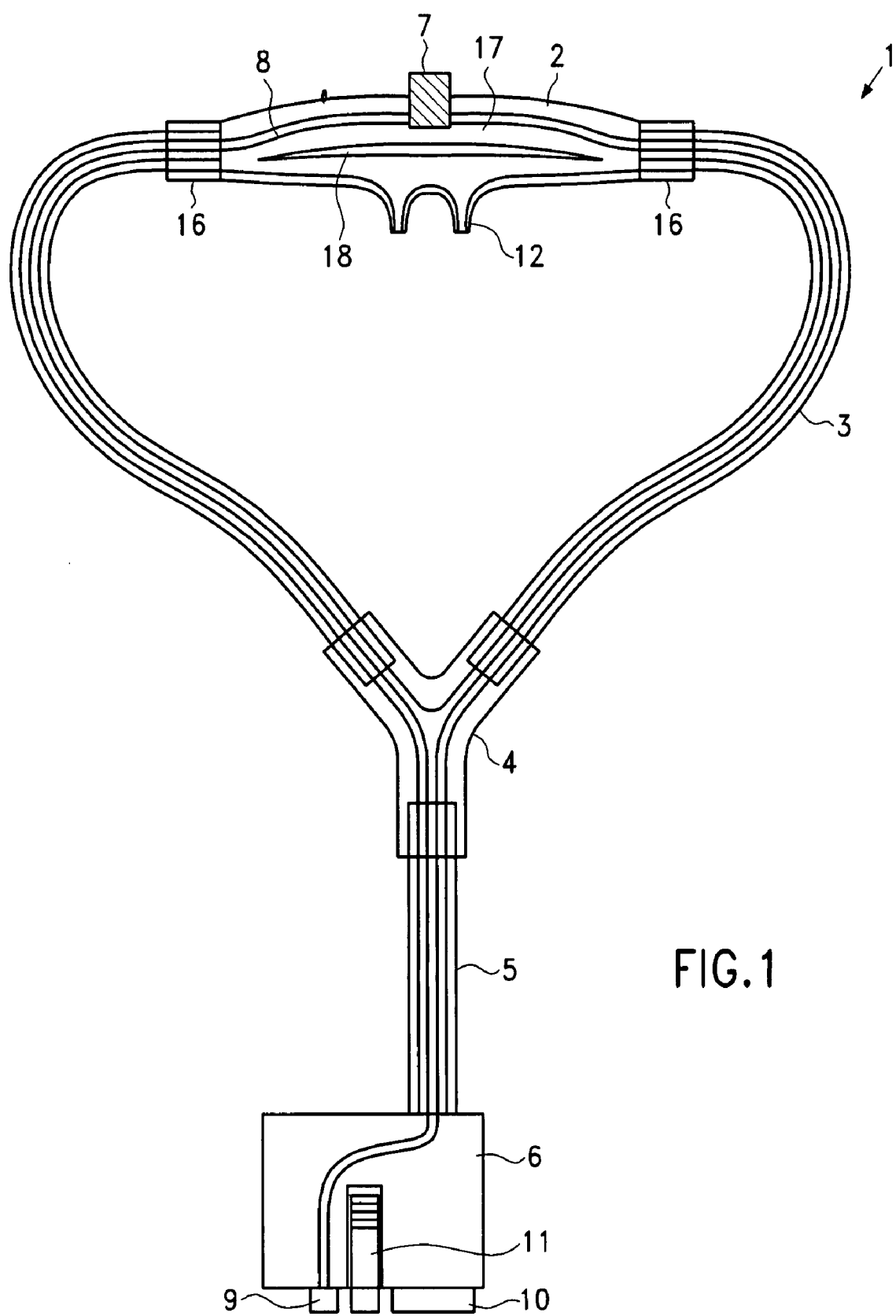
FIG. 1 shows a nasal cannula according to the invention, comprising a first embodiment of a nosepiece.

FIG. 1 shows a nasal cannula 1 according to the invention, comprising a first embodiment of a nosepiece 2. The nose piece 2 is supplied with compressed air via a forked tube 3, a Y-shaped element 4, a supply tube 5 and a connector 6. The nosepiece 2 includes two prongs 12 for administrating air into both nostrils of a user. Internal radius steps 16 compensate the difference between the internal and external radius of the forked tubes, thereby preventing abrupt changes to the cross-section of the airways.

The connector 6 comprises a pneumatic connector part 10, an electrical connector part 9 as well as a clamp 11. From the electrical connector part 9 a heating wire 8 is passed through the supply tube 5, the Y-shaped element 4, the right element of the forked tube 3, the right part of the nosepiece 2 to a temperature sensor 7, and from there through the left part of the nosepiece 2, the left element of the forked tube 3, the Y-shaped element 4 and the supply tube 5 back to the electrical connector part 9.

The clamp 11 engages a bushing provided for the connector 6 and secures the connector 6 against an unintended unplugging. A possible cross-section of the forked tube 3 and the supply tube 5 is explained in connection with FIG. 6. The supply tube 5 has a larger cross-section than the forked tube 3 because the supply tube 5 typically has to transport double the airflow, because the distance to be covered is greater and because the losses of comfort with a great tube thickness are smaller. The word forked tube has merely been chosen because the supply tube 5 is "forked" at the Y-shaped element 4.

With a view to approval requirements it may be necessary to shield the insulation of the heating wire 8 in the area of the nose piece 2 against the prongs 12 by an additional partition wall 18. In the area of the nosepiece 2 the heating wire 8 then extends in an additional lumen 17.

If nasal cannulas are to be used for pneumatically splinting the upper respiratory tract, there is a problem with respect to the noise development caused by the high airflows through the supply tubes and forked tubes, which are thin as compared to respiratory tubes. This results in a high flow velocity of the air, which generates noise at the edges. Therefore, it has been provided in the nasal cannula illustrated in FIG. 1 that the inner walls of the supply tube 5, of the Y-shaped element 4, of the two elements of the forked tube 3, of the nosepiece 2 and of the prongs 12 do not include any sharp edges and that specifically the inside of the transitions between these components do not form any steps or edges.

In another embodiment, component 7 may be a temperature switch 19, which one can regard as a temperature sensor having a poor resolution of one bit. The temperature switch can be realized, for example, by a bimetallic contact having a release temperature, for example, in the range of 30° C. to 50° C., specifically of 40° C. If the temperature of the temperature switch exceeds the release temperature, the heating circuit is interrupted.

Figure 2:
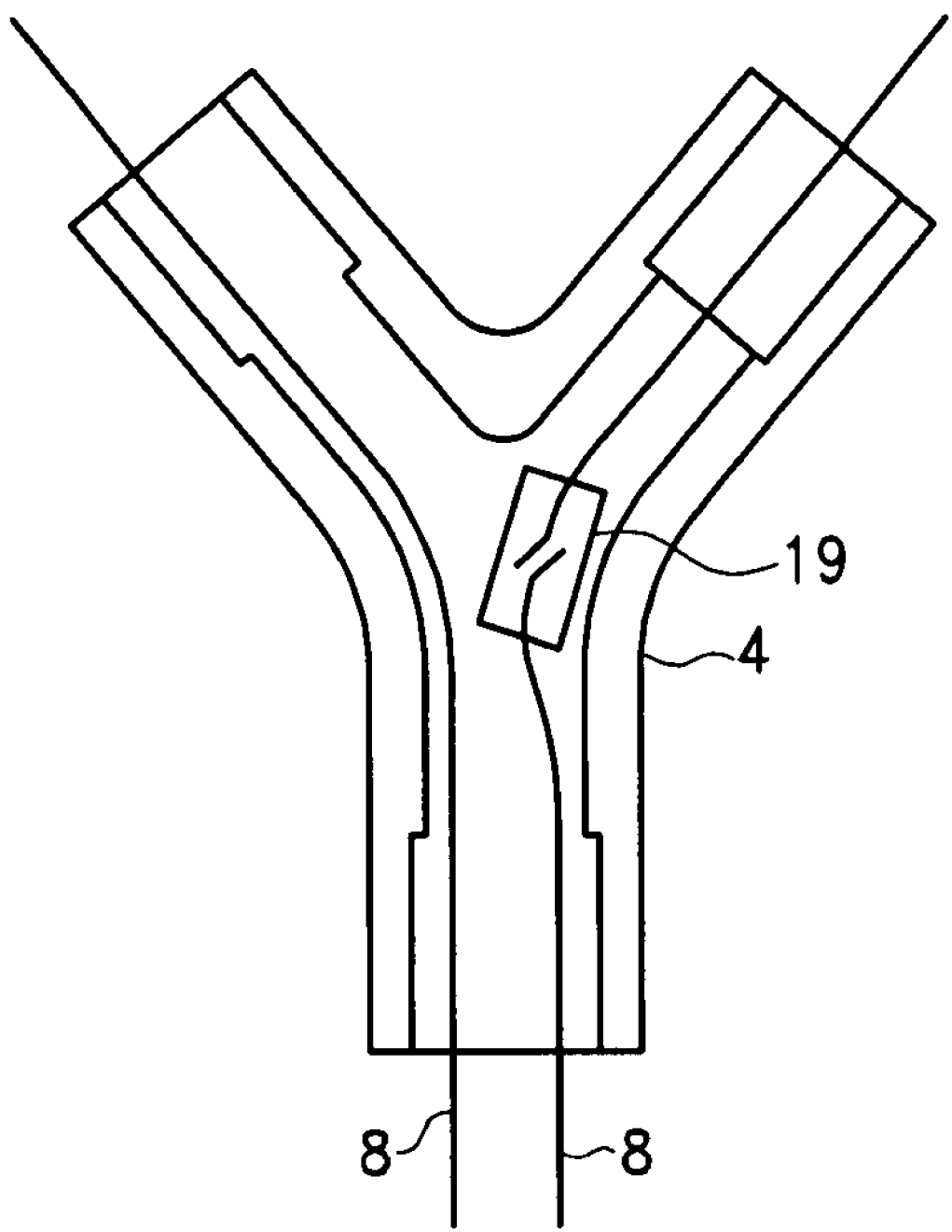
FIG. 2 shows a Y-shaped element comprising a temperature sensor.

Additionally or alternatively to component 7, a temperature sensor or switch 19 may be accommodated in the Y-shaped element 4, which is illustrated in FIG. 2. An additional temperature switch, e.g. a bimetallic contact having a release temperature of (50±10)° C., may represent a further protection against overheating, e.g. if the forked tube 3 and/or the supply tube 5 is/are kinked unintentionally. Above the release temperature the heating circuit is interrupted. The temperature switch 19 shown in FIG. 2 schematically represents a bimetallic contact.

If no temperature sensor 7 is provided in the nosepiece, a temperature sensor or switch 19 can effectively prevent condensation on its own because the supply tube 5 not heated by the patient's body ends in the Y-shaped element. Thus, the coldest spot and therefore the most susceptible point to condensation in the supply tube 5 is located between the compressor and the nosepiece 2. If the temperature of the coldest spot is kept above the thawing point, no condensation will take place. A shifting of the temperature sensor or switch into the Y-shaped element 4 may increase the wearing comfort of the nasal cannula 1, because the nosepiece 2 can be constructed lighter and smaller.

As the temperature of the air in the prongs 12 can be calculated by approximation from the temperature in the Y-shaped element, from the heating power and from the adjusted flow, if the geometry of the nasal cannula is predetermined, specifically if the lengths of the tubes and the diameters are predetermined, a shifting of the temperature sensor from the nosepiece 2 into the Y-shaped element 4 does not entail any considerable losses of comfort.

Figure 3:
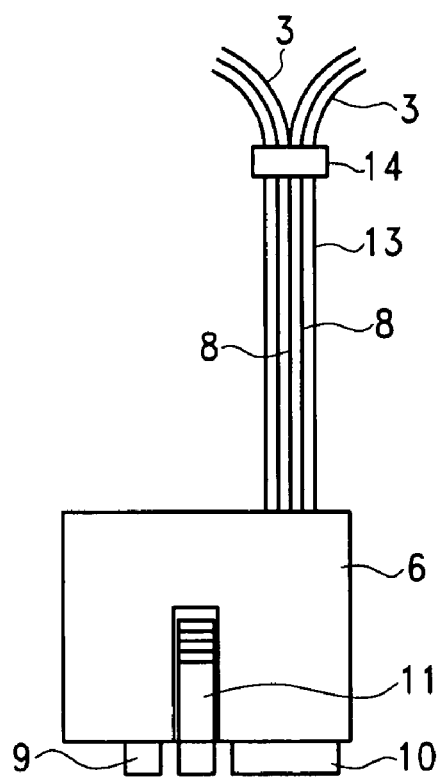
FIG. 3 shows a nasal cannula according to the invention comprising a double-lumen tube.

FIG. 3 shows a second embodiment of a nasal cannula, in which the supply tube 5 and the Y-shaped element 4 have been replaced by a double-lumen tube 13. The double-lumen tube consists of two forked tube elements which are mechanically connected to each other. In this embodiment, the Y-shaped element 4 is not applicable or is integrated in the connector 6 according to another perspective. At the point where the two forked tube elements diverge, no sharp edges are provided, but only wide radii. At this point a clip 14 may be provided, which prevents the double-lumen tube from further splicing apart. The division of an airflow to two forked tube elements may be realized in the connector 6 and is, thus, farther away from the prongs 12 so that the noise emission is lower.

Figure 4:
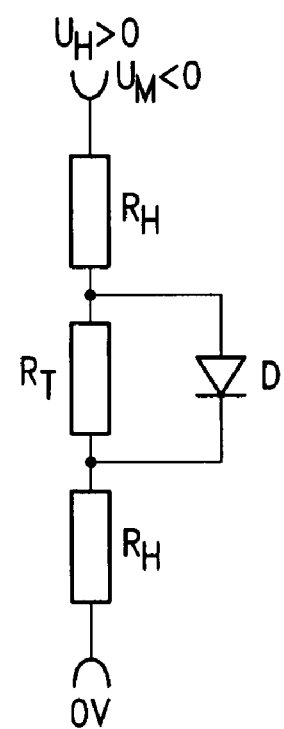
FIG. 4 shows a temperature measurement circuit.

FIG. 4 shows a possibility to read out a temperature sensor via two heating wires only. In the equivalent circuit diagram shown in FIG. 4, the two heating wires 8 are represented by the two resistors $R_H$. $R_T$ represents a two-terminal network with a temperature-dependent clamping characteristic.

In the simplest case, the resistor $R_T$ is merely a temperature-dependent resistor such as a Pt100 or a Pt1000. $R_T$ is large with respect to $R_H$. The heating wires typically have a resistance of 15Ω with great tolerances. If a positive heating voltage $U_H$ is administered to the three serially connected resistors, the temperature sensor is short-circuited by the parallel-connected diode D, so that substantially only the heating wires are heated. If a negative or a small measuring voltage $U_M$ is administered to the three serially connected resistors, the major part of the measuring voltage falls on the temperature sensor $R_T$. From this the temperature of the temperature sensor can be determined. The remaining voltage differences over the heating resistors can be calculated and allowed for.

However, it is also possible to use a temperature-dependent power source, which is, for example, provided in the form of the integrated circuit AD592, as a two-terminal network $R_T$. In this case, the diode D serves to bypass and, thus, protect the integrated circuit for the heating current. For example, a Schottky diode may be used for the diode D because of its small forward voltage. The direction of the measuring current is inverse to the heating current. Its amount depends on the temperature and on the integrated circuit as used and amounts to a few 100 μA. The particular advantage of this solution is that the wire resistance has practically no influence on the measuring result.

Beside the directly analogously transmitting sensors it is also possible to convert the temperature signal by modulating it onto the heating current. This can be accomplished both analogously and digitally and can be realized in custom-specific circuits. Such circuits are known, for example, in connection with telephones or baby phones for the modulation of audio-frequency signals to the operating voltage.

The polarity or level of the administered voltage may be switched over far more quickly than the thermal inertia of the system, so that the switching over between heating voltage $U_H$ and measuring voltage $U_M$ entails practically no change in temperature.

Figure 5:
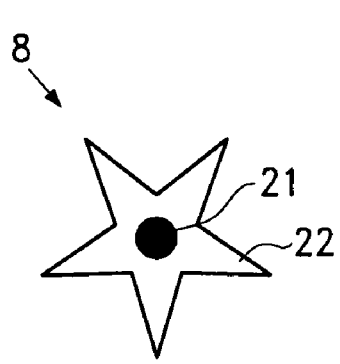
FIG. 5 shows the cross-section of a heating wire.

FIG. 5 shows a section through the embodiment of a heating wire 8. A metal wire 21 is embedded in an insulation 22. The insulation has a star-shaped cross-section with five triangular radials and is thus invariant with respect to rotations by 72°. The metal wire 21, too, may have a star-shaped cross-section. Each radial forms an elevation extending lengthwise of the wire. The elevations may also extend about the shell in a helical manner, with the length of one revolution being typically a multiple of the circumference of the insulation. It is the purpose of the star-shaped insulation to increase the surface of the wire so as to reduce the thermal resistance with respect to the ambient air. Moreover, even if the tube is kinked, air should flow around the heating wire, if possible, on all sides so as to prevent it from overheating and melting into the surrounding tube. The triangular radials of the cross-section thereby expand the kink site of a tube, with the contact surface between the tube and the insulation being small and the thermal resistance thus remaining large. The metal wire 21 may have a diameter of approximately 0.3 mm and a circle just about enclosing the apexes of the cross-section may have a diameter of 1 mm.

Figure 6:
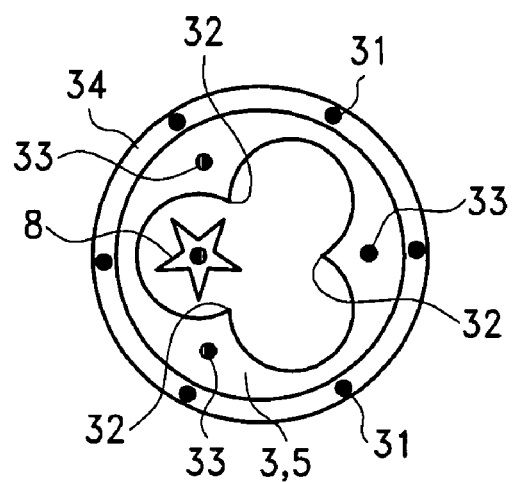
FIG. 6 shows the cross-section of a tube comprising a heating wire.

FIG. 6 shows a section through a tube, which may be a forked tube 3 or a supply tube 5. Typically, both types of tubes mainly differ from one another by their diameter. The inner shell of the tube includes projections 32, which serve to expand the jacket of the tube also at kink sites so that the airflow is not fully constricted despite the kink. On the outer circumference of the tube and/or in the tube material itself, specifically in projections 32, stabilizing filaments 31 and 33, respectively, are mounted or incorporated to reduce a linear expansion of the tube. The stabilizing filaments 31 and 33 may be incorporated into the tube material, specifically into the projections 32 during the production process. The stabilizing filaments 31 and 33 may be made of an artificial or natural fibrous material, a synthetic material or metal. The reason for the provision of the stabilizing filaments is that heat-resistant PVC is too rigid, so that therefore, for example, TPE or silicone have to be used. The latter materials are strongly expandable, which may be undesired in the longitudinal direction because tensile forces occurring in this case have to be absorbed by the heating wire, thereby subjecting it and terminals thereof to mechanical stress. As the tubes are operated at maximum pressures of a few 100 millibar, a stabilization in a radial direction does not seem to be necessary.

If the stabilizing filaments, specifically those in projections 32, are made of an electrically conductive material, specifically of metal, possibly surrounded by a thermally resistant, not necessarily biocompatible, electrical insulation, they can be employed for heating and replace the heating wire 8. Thus, problems with non-biocompatible insulating materials may be bypassed.

Finally, the forked tube 3 and/or the supply tube 5 may be surrounded by a thermal insulation 34. This insulation 34 should not be too thick because specifically a thin forked tube means comfort and a thick insulation means a loss of comfort. On the other hand, an insulation may render the surface of the tubes soft and thus more comfortable. From a technical point of view the insulation has the advantage that it reduces the heating power, which has to remain under 15W even in the case of a defect, if the power control fails, or if the entire supply voltage is administered. A reduction of the heating power therefore makes the use of less exactly tolerated and, thus, more inexpensive heating wires or longer tubes possible. The nasal cannulas currently projected require, in fact, a maximum heating power of nearly 15W.

FIGS. 7, 9 and 11 show three perspective views of a second embodiment of a nosepiece 42. FIGS. 8 and 10 show sections along lines Z-Z and M-M, respectively. The second embodiment of the nosepiece 42 differs from the embodiment of nosepiece of 2 merely with respect to the quality. To reduce the noise emission, nosepiece 2 is more bulged, i.e. the clear cross-sectional area increases more strongly from the tube connections to the prongs. This reduces the flow velocity of the air so as to keep the noise emission low. The reduction of the flow resistance by increasing the cross-sectional area in the nosepiece is negligent, because the flow resistance is mainly defined by the thickness of the forked tube 3. At present, three prototypes each showing a different increase of the cross-sectional area are in preparation. Measurement results are not yet available.

The nosepiece 42 comprises tube connections 44, tube transition regions 45, connection pieces 47, prongs 52 having annular knobs 53 as well as a central connection piece 48. As can be seen in FIG. 11, an internal radius step 46 is respectively located between the tube transition regions 45 and the tube connections 44, which just about compensates the difference between the internal and the external radius of the forked tube 3 so as to obtain a transition as even as possible between the inner surface of the forked tube 3 and the nosepiece 42. For this purpose, the projections 32 at the ends of the forked tube 3 may be removed, or corresponding projections may be formed on the inner surface of the nosepiece 42.

As can also be seen in FIG. 11, the clear cross-sectional area in the tube transition region 45 is expanded.

As can readily be seen in FIG. 9, the transition regions 54 between the prongs 52 and the connection pieces 47 are generously radiused so as to reduce the noise emission. In the prototype this radius is, for example, externally 4.3 mm. The outer diameter of the prongs in the proximity of the connection piece is 5.5 mm and in the proximity of the aperture 5 mm. The wall thickness is approximately 0.5 mm.

The transition region between the central connection piece 48 and the prongs 52 is likewise rounded off, wherein the external radius is also in the range between 4 and 5 mm.

A sectional view of the indentation 43 in the central connection piece 48 is illustrated in FIGS. 8 and 10 while a top view is shown in FIG. 9. It serves the adjustment of a defined flow resistance between the left and the right side of the nose glasses. As is shown in FIG. 1, the nasal cannula is mirror-symmetrical. This also applies in most cases to the user. As long as there is a mirror symmetry, no air flows through the central connection piece 48. The symmetry can be interrupted, for example, by a kink in the left or right forked tube 3 or by the user having a cold so that one nostril is blocked. In the former case it is desirable, on the one hand, that both prongs are supplied by the tube that is still open. On the other hand, the kinked forked tube is, of course, not entirely closed. The higher the pressure drop at the kinked forked tube, the greater is the cooling airflow for the heating wire 8. To slightly increase the pressure drop at the kinked forked tube, a pressure drop at the central connection piece 48 may be desirable. If one nostril is blocked, it is desirable to apply more air via the other prong. In this case, too, an airflow through the central connection piece 48 is desirable.

FIGS. 9, 10 and 11 also illustrate the temperature sensor 7.

In FIG. 12 the Y-shaped element 4 is shown in an enlarged manner. One recognizes the two forked tube connections 91 at the top and the connection 93 for the supply tube at the bottom. The transition region 95 between the two forked tube connections is rounded off and has in one embodiment a radius of 1 mm. In this embodiment the forked tubes and the supply tube have, for the purpose of comparison, an internal radius (without projections 32) of 3 and 5 mm, respectively. The rounding of the transition region 95 is specifically important if asymmetric flow ratios exist, for example, because of a kinked forked tube. All connections have internal radius steps 92 and 94 so as to compensate the difference between the internal radius and the external radius of the connected tubes. The internal radius steps may either have projections corresponding to the projections 32 in the connected tubes and/or the projections 32 may be removed at the ends of the tubes.

Although the invention was explained above in connection with the gas air, of course, any other breathable gas mixture may be used. Apart from this, the composition of air, for example, in respect of its water and oxygen content is not exactly defined.

The invention was explained in more detail by means of preferred embodiments above. A person skilled in the art will appreciate, however, that various alterations and modifications may be made without departing from the gist of the invention. Therefore, the scope of protection will be defined by the accompanying claims and their equivalents.

The following list of reference numerals may assist in identifying the elements shown in the drawings.

1 nasal cannula
2 nosepiece
3 forked tube
4 Y-shaped element
5 supply tube
6 connector
7 temperature sensor
8 heating wire
9 electrical connector part
10 pneumatic connector part
11 clamp
12 prong
13 double-lumen tube
14 clip
16 internal radius step
17 additional lumen
18 partition wall
19 temperature switch
21 metal wire
22 insulation
31 stabilizing filament
32 projection
33 stabilizing filament
34 thermal insulation
42 nosepiece
43 indentation
44 tube connection
45 tube transition region
46 internal radius step
47 connection piece
48 central connection piece
52 prong
53 knob
54 prong transition region
91 forked tube connection
92 internal radius step
93 supply tube connection
94 internal radius step
95 transition region

The invention claimed is:

1. A nasal cannula for an anti-snoring or PAP apparatus, comprising:
a forked tube pneumatically connected to apertures, which are embodied and positioned in such a way that air can be administered into the nose of a user via these apertures,
characterized by:
a heating wire extending in the forked tube in such a way that the heating wire can heat the air supplied through the forked tube.

2. The nasal cannula according to claim 1, wherein a temperature sensor is mounted in the proximity of the apertures so that the temperature sensor can measure the temperature of the air administered via the apertures.

3. The nasal cannula according to claim 2, wherein the temperature sensor is connected to the heating wire in such a way that it can be supplied with electric energy via the heating wire and that the temperature signal of the temperature sensor can also be read out via the heating wire.

4. The nasal cannula according to claim 3, wherein the temperature sensor is a digital temperature sensor modulating its temperature signal onto the voltage supplied to the temperature sensor via the heating wire.

5. The nasal cannula according to claim 1, wherein the heating wire has a wire-shaped metal core surrounded by an insulation, the external shell of which comprises elevations and recesses.

6. The nasal cannula according to claim 1, wherein the heating wire has a wire-shaped metal core surrounded by an insulation, the external shell of which comprises elevations and recesses, wherein a temperature sensor is mounted in the proximity of the apertures so that the temperature sensor can measure the temperature of the air administered via the apertures.

7. The nasal cannula according to claim 1, wherein the heating wire has a wire-shaped metal core surrounded by an insulation, the external shell of which comprises elevations and recesses, wherein the temperature sensor is a digital temperature sensor modulating its temperature signal onto the voltage supplied to the temperature sensor via the heating wire.

8. The nasal cannula according to claim 1, wherein the heating wire has a wire-shaped metal core surrounded by an insulation, the external shell of which comprises elevations and recesses, wherein the shell of the insulation includes elevations with triangular cross-sections which extend approximately in the longitudinal direction of the heating wire, so that the insulation has altogether a star-shaped cross-section.

9. The nasal cannula according to claim 1, wherein the heating wire has a wire-shaped metal core surrounded by an insulation, the external shell of which comprises elevations and recesses, wherein the metal core includes elevations and recesses on its shell.

10. The nasal cannula according to claim 1, wherein the forked tube comprises stabilizing filaments.

11. The nasal cannula according to claim 1, characterized in that two elements of the forked tube are mechanically connected to a double-lumen tube at a connector-sided end.

12. The nasal cannula according to claim 1, wherein the forked tube is pneumatically connected to a pneumatic connector part of a connector and wherein the heating wire is electrically connected to an electrical connector part of the connector.

13. The nasal cannula according to claim 1, wherein the apertures are formed by prongs approximately in the center of a nosepiece, wherein a left element of the forked tube is pneumatically connected to the left side of the nosepiece and a right element of the forked tube is pneumatically connected to the right side of the nosepiece and the heating wire extends from the left element of the forked tube through the interior of the nosepiece to the right element of the forked tube.

14. The nasal cannula according to claim 1, characterized in that two elements of the forked tube are mechanically connected to a double-lumen tube at a connector-sided end, wherein the forked tube is pneumatically connected to a pneumatic connector part of a connector and wherein the heating wire is electrically connected to an electrical connector part of the connector, wherein the apertures are formed by prongs approximately in the center of a nosepiece, wherein a left element of the forked tube is pneumatically connected to the left side of the nosepiece and a right element of the forked tube is pneumatically connected to the right side of the nosepiece and the heating wire extends from the left element of the forked tube through the interior of the nosepiece to the right element of the forked tube.

15. The nasal cannula according to claim 1, wherein the forked tube comprises stabilizing filaments, wherein two elements of the forked tube are mechanically connected to a double-lumen tube at a connector-sided end.

16. The nasal cannula according to claim 1, wherein the heating wire has a wire-shaped metal core surrounded by an insulation, the external shell of which comprises elevations and recesses, wherein the metal core includes elevations and recesses on its shell, wherein the forked tube comprises stabilizing filaments.

17. The nasal cannula according to claim 1, wherein a temperature sensor is mounted in the proximity of the apertures so that the temperature sensor can measure the temperature of the air administered via the apertures, wherein the temperature sensor is connected to the heating wire in such a way that it can be supplied with electric energy via the heating wire and that the temperature signal of the temperature sensor can also be read out via the heating wire, wherein the temperature sensor is a digital temperature sensor modulating its temperature signal onto the voltage supplied to the temperature sensor via the heating wire.

18. A nasal cannula having a nosepiece for an anti-snoring or PAP apparatus, comprising:
    a forked tube pneumatically connected to apertures, which are embodied and positioned in such a way that air can be administered into the nose of a user via these apertures,
    characterized by:
    a heating wire extending in the forked tube in such a way that the heating wire can heat the air supplied through the forked tube
    further comprising a nosepiece for a nasal cannula comprising:
        a connection point for mounting a forked tube;
        wherein the connection point includes an internal radius step at one end of the connection point the height of which just about corresponds to half the difference between the inner and outer diameter of the forked tube so as to obtain an even transition between the interior of the forked tube and the interior of the nosepiece upon mounting a forked tube at the connection point.

19. The nasal cannula having the nosepiece of claim 18, for nasal cannulas, further comprising:
    a prong for administrating air into a nostril of a user; and
    a connection piece which mechanically and pneumatically connects the prong to the connection point,
    characterized in that the transition region between the prong and the connection piece has a radius in a plane which is defined by the prong and the connection piece, the radius being larger than the radius of the prong.

20. The nasal cannula having a nosepiece of claim 19, further comprising:
    two prongs for administrating air into each nostril of a user;
    a central connection piece which mechanically and pneumatically connects the two prongs;
    two tube connections; and
    two connection pieces, wherein each connection piece mechanically and pneumatically connects one prong to one tube connection;
    characterized in that;
    the central connection piece includes an indentation so that the area of the clear cross-section of the central connection piece is smaller than the area of the clear cross-sections of the two connection pieces.

21. The nasal cannula having the nosepiece of claim 18, further comprising:
    two prongs for administrating air into each nostril of a user;

a central connection piece which mechanically and pneumatically connects the two prongs;

two tube connections; and two connection pieces, wherein each connection piece mechanically and pneumatically connects one prong to one tube connection;

characterized in that the central connection piece includes an indentation so that the area of the clear cross-section of the central connection piece is smaller than the area of the clear cross-sections of the two connection pieces.

22. The nasal cannula having the nosepiece according to claim 21, for nasal cannulas, comprising:

characterized in that a transition region between the central connection piece is rounded off in a plane which is defined by the two prongs, wherein the radius of this transition region is larger than the radius of the prongs.

23. The nasal cannula having a nosepiece according to claim 18, for nasal cannulas, further comprising:

two prongs for administrating air into each nostril of a user;

a central connection piece which mechanically and pneumatically connects the two prongs;

characterized in that the transition region between the central connection piece is rounded off in a plane which is defined by the two prongs, wherein the radius of this transition region is larger than the radius of the prongs.

24. A nasal cannula having a Y-shaped element for an anti-snoring or PAP apparatus, comprising:

a forked tube pneumatically connected to apertures, which are embodied and positioned in such a way that air can be administered into the nose of a user via these apertures, characterized by:

a heating wire extending in the forked tube in such a way that the heating wire can heat the air supplied through the forked tube further comprising a Y-shaped element for nasal cannulas comprising:

two forked tube connections; and a supply tube connection, the Y-shaped element mechanically and pneumatically connecting all three tube connections, characterized in that each of the two forked tube connections includes an internal radius step at one end of the forked tube connection the height of which just about corresponds to half the difference between the inner and outer diameter of the forked tube so as to obtain an even transition between the interior of the forked tube and the interior of the Y-shaped element upon mounting a forked tube at a forked tube connection.

25. The nasal cannula having a Y-shaped element according to claim 24, characterized in that the supply tube connection includes an internal radius step at one end of the supply tube connection the height of which just about corresponds to half the difference between the inner and outer diameter of the supply tube so as to obtain an even transition between the interior of the supply tube and the interior of the Y-shaped element upon mounting a supply tube at the supply tube connection.

26. The nasal cannula having a Y-shaped element according to claim 25, characterized in that the transition region is rounded off between the two forked tube connections in the interior of the Y-shaped element, wherein the radius in this transition region in a plane which is defined by the two forked tube connections is larger than a tenth of the clear cross-section of a forked tube connection.

27. The nasal cannula having a Y-shaped element according to claim 24, characterized in that the transition region is rounded off between the two forked tube connections in the interior of the Y-shaped element, wherein the radius in this transition region in a plane which is defined by the two forked tube connections is larger than a tenth of the clear cross-section of a forked tube connection.

28. A method for avoiding condensation in nasal cannulas, comprising the steps of:

supplying a gas to the nasal cannula;

administrating the gas through apertures in the nasal cannula;

heating the gas as it flows through the tubes of the nasal cannula incorporating a temperature sensor, which measures the temperature in the proximity of the apertures, is supplied via heating wires with electric energy for heating the gas and that the heating wires are used to transmit the sensor signal; measuring the temperature in the proximity of the apertures for administrating the gas; and controlling the heating power so as to avoid a condensation in the nasal cannula.

29. The method according to claim 28, further comprising the steps of:

measuring the temperature in the proximity of the apertures for administrating the gas; and controlling the heating power so as to avoid a condensation in the nasal cannula.

30. The method according to claim 28, further comprising the steps of: incorporating a temperature sensor, which measures the temperature in the proximity of the apertures, is supplied via heating wires with electric energy for heating the gas and that the heating wires are used to transmit the sensor signal.

31. The method according to claim 28, further comprising the step of:

measuring the temperature in the proximity of the apertures for administrating the gas; and controlling the heating power so as to avoid a condensation in the nasal cannula.

* * * * *